United States Patent [19]
Bell

[11] Patent Number: 4,938,353
[45] Date of Patent: Jul. 3, 1990

[54] CONTAINER AND DISPENSER FOR ANEURYSM CLIPS

[75] Inventor: Richard L. Bell, Marshfield, Mass.

[73] Assignee: Codman & Shurtleff, Inc., Randolph, Mass.

[21] Appl. No.: 428,255

[22] Filed: Oct. 27, 1989

[51] Int. Cl.⁵ .................... B65D 83/00; B65D 85/00
[52] U.S. Cl. ................................ 206/339; 220/82 A
[58] Field of Search ........ 206/338, 339, 490, 340–347, 206/382, 562, 564

[56] References Cited
U.S. PATENT DOCUMENTS

| 1,957,377 | 5/1934 | Whittle | 206/490 X |
| 4,151,913 | 5/1979 | Freitag | 206/382 X |
| 4,508,216 | 4/1985 | Kelman | 220/82 A |
| 4,821,878 | 4/1989 | Jones | 206/339 |

Primary Examiner—William Price
Attorney, Agent, or Firm—Donal B. Tobin

[57] ABSTRACT

A container and dispenser for aneurysm clips is shown which allows the aneurysm clips to be magnified as they are displayed to the user to facilitate easy removal of the clip from the container. The container includes a base preferably made of silicone or some other rubber like material with slits for holding the jaws of an aneurysm clip and a platform for raising the coil and arms of a clip above the top surface of the base. The container also includes a generally disc shaped magnifier housing for a containing a plurality of magnifying lenses and a shaft extending into a corresponding bore in the base. A locking ring attached to the shaft is used to control the distance the magnifier housing can be moved above the top surface of the base so that the clips will be in focus for the user.

15 Claims, 5 Drawing Sheets

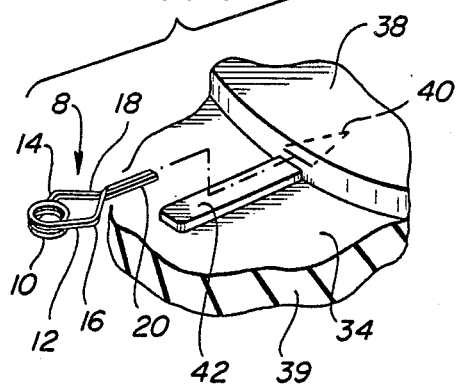
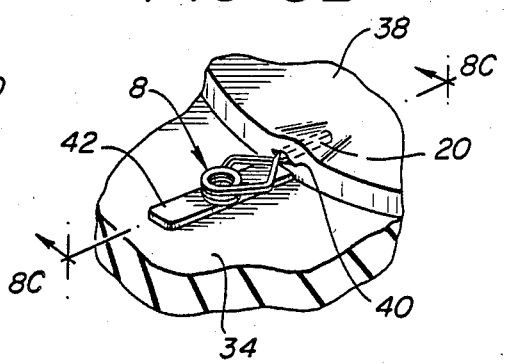
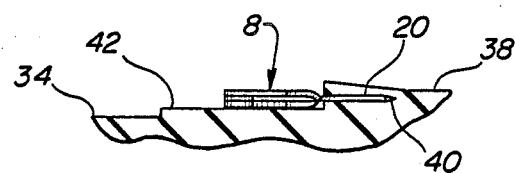
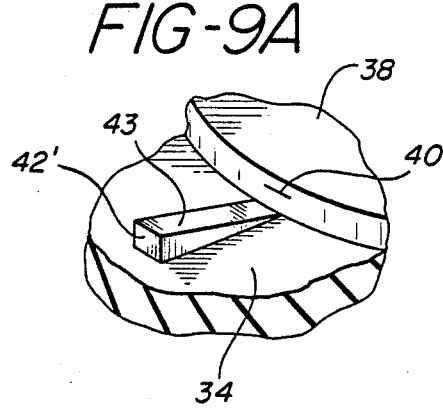
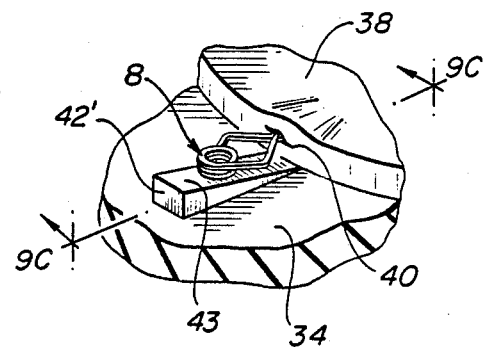
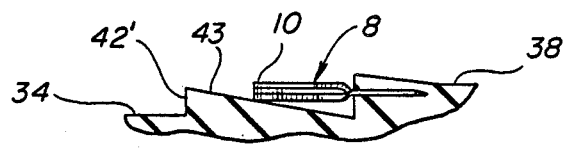

CONTAINER AND DISPENSER FOR ANEURYSM CLIPS

The present invention relates to a container and dispenser for aneurysm clips and, more particularly, to a container which includes magnifying lenses to permit the user to better visualize small aneurysm clips so that they can be quickly and efficiently removed from the container and dispenser with a suitable aneurysm clip applying instrument.

BACKGROUND OF THE INVENTION

An aneurysm is a permanent dilitation of the wall of a blood vessel usually caused by weakening of the wall as a result of some pathological condition. In layman's terms, the wall weakens and pressure in the vessel causes the wall to expand into a balloon appendage in the side of the vessel. The balloon often has a neck portion extending from the wall and an expanded portion connected to the neck, although an aneurysm may take various shapes.

One way of treating an aneurysm is to apply a clip to seal off the neck portion of the aneurysm close to the blood vessel wall so that blood pressure will not be exposed to the weakened expanded portion of the aneurysm. Thus, the possibility of the aneurysm bursting is reduced and hopefully eliminated. It is hoped that the clip will seal off the weakened portion of the wall so that blood vessel can heal. An aneurysm clip 8 of the kind stored in the container and dispenser of the present invention is shown, for example, in U.S. Pat. No. 3,827,438 and is shown generally in FIG. 8A and the disclosure of this patent, as it relates to aneurysm clips is incorporated into this application. These kinds of clips 8 generally have a torsion spring coil 10 with a first arm 12 extending from one end of the coil 10 and second arm 14 extending from the other end of the coil 10. Each of the first and second arms 12 and 14 has a shoulder portion 16, a cross over portion 18 and a jaw portion 20. When the shoulder portions are moved together (with a special forcep), jaw portions 20 move away from each other toward the open position so that an aneurysm can be grasped between the two confronting jaw portions to seal off an aneurysm.

Certain aneurysm clips are very small. Their small size makes them difficult to grasp properlY in a special forcep called an aneurysm clip applier. It would be desirable to have a container and dispenser for aneurysm clips particularly very small size aneurysm clips to make it easier for the user to visualize and properly grasp the clip.

SUMMARY OF THE INVENTION

The present invention provides a container and dispenser for plurality of aneurysm clips particularly small aneurysm clips which may be hard to grasp with a forceps. The container has a base for retaining a number of clips, a clip retainer, preferably a slit in the base, for holding at least a portion of each clip. A number of platforms are aligned on the base with the clip retainers for separating at least a portion of each clip from the base to facilitate grasping of a clip in an instrument. The container and dispenser also includes a magnifier housing with at least one lens positioned to allow the user to visualize the platforms through the lens. A cooperating mechanism preferably a shaft on the magnifier housing and a bore on the base connects the base and the magnifier housing together to permit the magnifier housing to be moved between a first position close to the base and a second position separated from the base and the platforms on the base by the focal distance of the lens to bring the clips into focus for the user to facilitate removal of the clip.

The base is preferably made of a resilient material like silicone. The magnifier housing is preferably made of a plastic material and the lenses are preferably molded into the magnifier housing. The optical axis of each lens is aligned generally perpendicular to the surface of each platform on which each lens sits. Preferably the base is a right circular cylinder and the clip retainers and platforms are integral with the base. The clip retainer is preferably a slit in the base for retaining a portion of the clip usually the jaws of a clip.

The platforms can be generally rectangular in shape raised above the surrounding top surface of the base. Alternatively, the platforms can be wedge shaped having an angled surface with a height which increases as one advances from the center of the base toward the perimeter of the base.

The shaft of the housing is usually equipped with a stop which abuts the inside of the base top surface to control the distance which the magnifier housing may be moved away from the top surface of the base. That distance is the focal distance of the lenses.

In another embodiment a portion of the top surface of the base is disposed at an angle to the surface of the platform in which a clip rests to make it easier to align the forceps as the user attempts to remove a clip from the container and dispenser of the present invention.

These and other features and advantages of the present invention will become more apparent from the following detailed description of the preferred embodiments taken in conjunction with the following drawings.

BRIEF DESCRIPTION OF THE DRAWINGS

FIG. 8A shows a partial perspective view of a segment of one embodiment of the container of the present invention;

FIG. 8B shows the same thing as FIG. 8A with a clip held in place;

FIG. 8C shows a side elevational view partly in section taken along line 8C—8C in FIG. 8B;

FIG. 9A shows a partial perspective view of a segment of another embodiment of the container of the present invention;

FIG. 9B shows the same thing as FIG. 9A with a clip held in place;

FIG. 9C shows a side elevational view partly in section taken along line 9C—9C in FIG. 9B;

DETAILED DESCRIPTION OF THE PREFERRED EMBODIMENT

Figure 1:
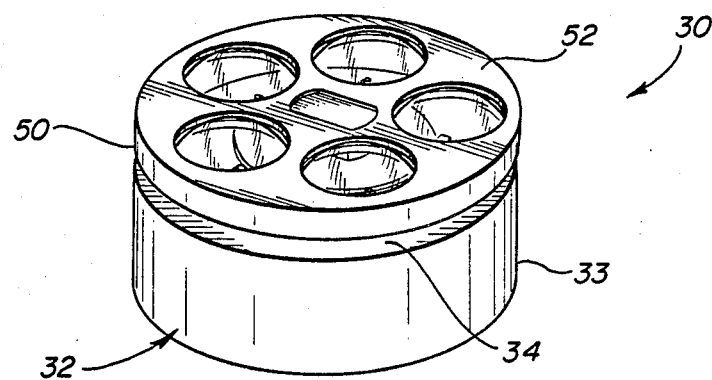
FIG. 1 shows a perspective view of the container and dispenser of the present invention in the closed position.
Figure 4:
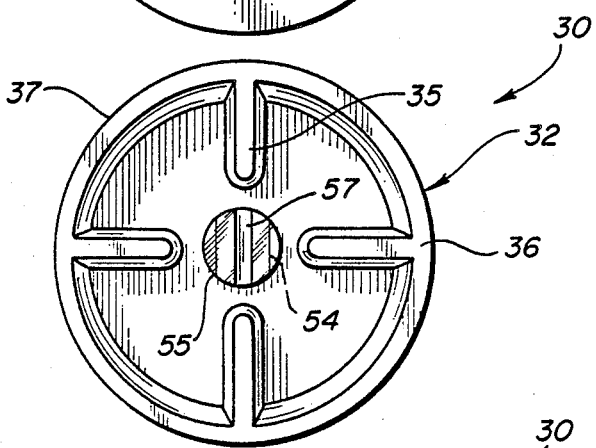
FIG. 4 shows a bottom plan view partly in section, of the container of FIG. 3.
Figure 5:
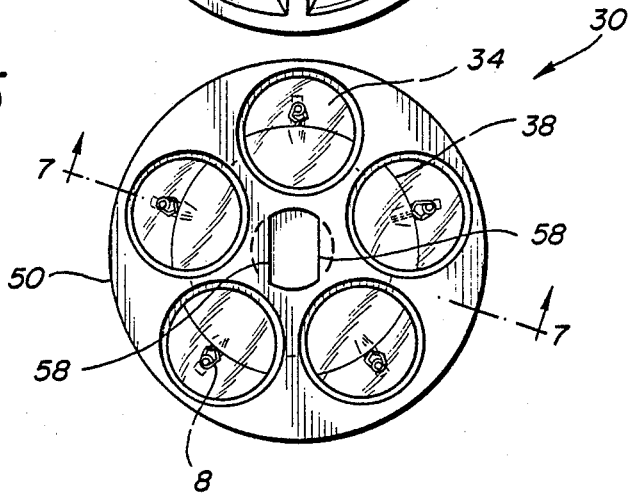
FIG. 5 shows a top plan view of the container of FIG. 2.

Referring now to FIG. 1 there is shown a perspective view of the container and dispenser 30 of the present invention including a base 32 which is preferably made of a resilient material like silicone or some other rubber like material. The base is preferably generally cYlindrical in shape with a circular perimeter 33 and a top surface 34 and bottom surface 36. The base need not be cylindrical but may be any convenient shape including elliptical or rectangular. As shown in FIG. 4, base 32 may be hollow with reinforcing ribs 35 and a thin top portion 39 and thin surrounding wall 37.

Figure 6:
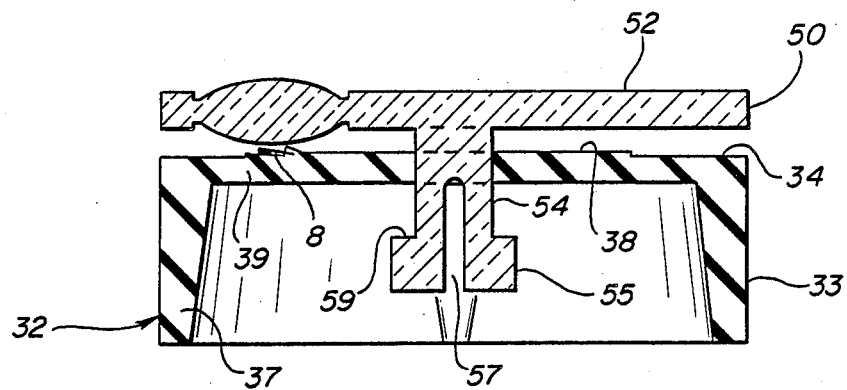
FIG. 6 shows a side sectional view taken along line 6—6 of FIG. 3.
Figure 7:
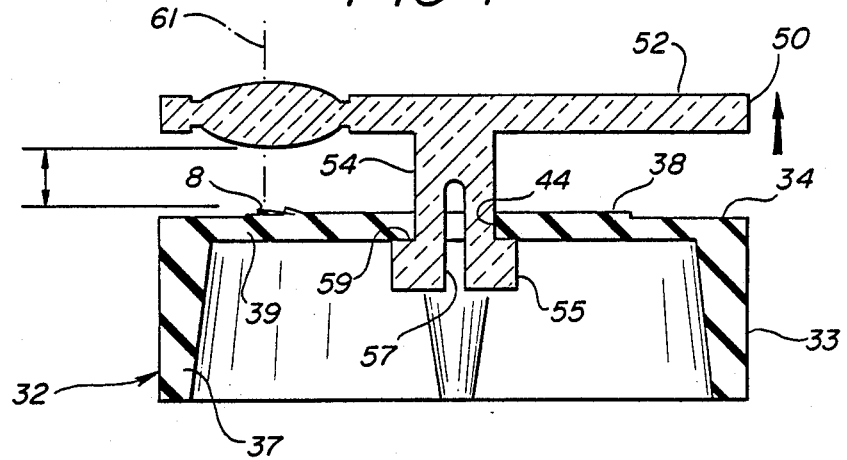
FIG. 7 shows a side sectional view taken along line 7—7 of FIG. 5.

As shown in FIGS. 6 and 7 top surface 34 of base 32 includes a generally coaxially aligned upstanding boss 38. Boss 38 has a plurality of slits 40 into which the jaws 20 of aneurysm 8 may be inserted. (See FIG. 8B) Slits 40 are preferably aligned generally parallel to top surface 34 but any convenient orientation that holds clip 8 in place is satisfactory. The boss 38 is preferably integral with and made of the same material as base 32. The material of base 32 and boss 38 are preferably high friction so that jaws 20 of clip 8 will be held in position by the confronting surfaces of slit 40.

In the preferred embodiment, the boss 38 is preferably a circular cylinder aligned coaxially with base 32 and slits 40 are placed equiangularly around the perimeter of boss 38. Those skilled in the art will recognize that boss 38 may be any convenient shape and can hold any convenient number of clips. Boss 38 could be triangular shaped with one clip at each point of the triangle or rectangular or star shaped or like a gear with multiple teeth with a slit to hold a clip at each point of the triangle, rectangle, star or gear teeth. The variety of shapes mentioned in this paragraph are meant to be illustrative rather than limiting and any convenient shape could be used.

Figure 2:
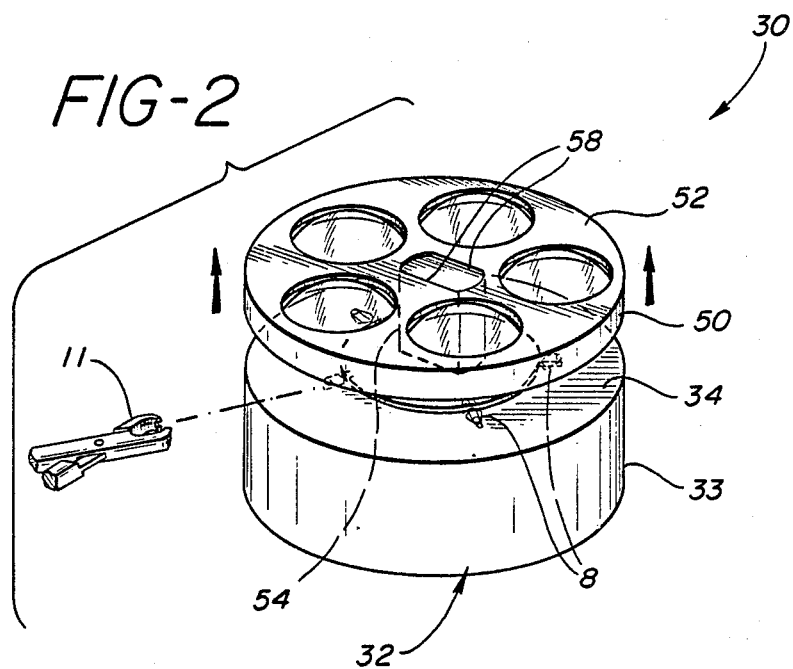
FIG. 2 shows a perspective view of the apparatus of FIG. 2 in the open position.
Figure 3:
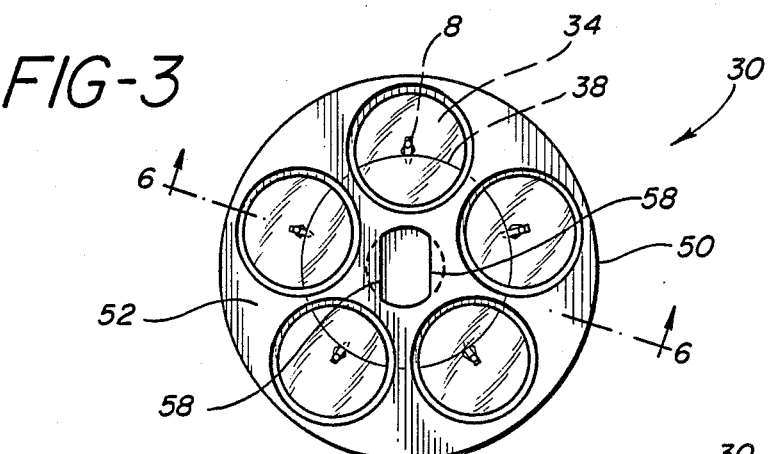
FIG. 3 shows a top plan view of the container of FIG. 1.

In the preferred embodiment, as shown in FIGS. 8A, 8B and 8C a platform 42 extends generally radially outwardly from each slit 40 to raise the coil 10 and arm portions 16 of clip 8 above adjacent top surface 34 of base 32 to make it easier for the user to grasp clip 8 with a aneurysm clip applier 11 (see FIG. 2). Platform 42 can be a small generally rectangular platform raised above top surface 34 of base 32. Platform 42 preferably has a width less than the width of shoulder portions 16 to make it easier to grasp clip 8 with forceps.

Base 32 has a generally coaxially aligned bore 44 extending all the way through top surface 34 of base 32.

Bore 44 is equipped with an anti-rotation feature whose purpose will be explained later in the application. This could be a generally elliptical shape for bore 44 or alternatively, bore 44 could be circular with a key way extending radially outwardly from the bore. Preferably the cross section of bore 44 is circular with two opposed flattened portions.

Magnifier housing 50 preferably includes a generally cylindrical disc 52 and a shaft 54 extending coaxially from one side of disc 52. Shaft 54 has a flange 55 extending radially outward around the part of shaft 54 most removed from disc 52. Flange 55 and shaft 54 may be partially slotted at slot 57 to permit radial flexibility so that shaft 54 may be inserted through bore 44. Top surface 59 of flange 55 contact the inside surface of top portion 39 to provide a stop for the movement of magnifier housing 50 with respect to base 32. Alternatively, flange 55 could be replaced by a locking ring placed on shaft 54 at the proper location to control the separation of magnifier housing 50 from base 32. The cross section of shaft 54 matches that of a bore 44. If bore 44 is elliptical shaft 54 is similarly elliptical so that magnifier housing 50 will not readily rotate with respect to base 32 when magnifier housing 50 and base 32 are assembled. Preferably shaft 54 has a circular cross section with two opposed flattened portions 58. (see FIG. 2)

A plurality of lenses 60 are placed equiangularly around magnifier housing disc 52. Lenses 60 are aligned with platforms 42 on base 32. Lenses 60 are preferably molded as one piece with disc 42 but may be separate pieces glued into holes in disc 52.

Each lens 60 has an optical axis 61 (see FIG. 7) aligned perpendicular to the top surface of its corresponding platform 42.

The container and dispenser of the present invention is used as follows. Shaft 54 is inserted in bore 44 with each lens 60 aligned with a corresponding platform 42. Shaft 54 will not readily rotate in bore 44. Magnifier housing 52 is then separated from top surface 34 of base 32 the maximum desired amount and one clip 8 is placed in each one of slits 40 in boss 38 resting on each platform 42 (see FIGS. 8A, 8B and 8C). Magnifier housing 52 is then collapsed onto or adjacent top surface of platform 42 and the whole package is then sterilized and encapsulated in a sterile package, preferably a blister pack, for shipment.

When the user wishes to remove an aneurysm clip from container and dispenser 30, the user removes the blister pack, slides magnifier housing 52 from its first position against top surface 34 of base 32 (see FIG. 1) to a second position separated from the top surface 34 by an amount controlled by the position of flange 55 which is selected to equal the focal distance of lenses 60 (see FIG. 2). Thus, the user can easily visualize a magnified clip for easy removal with an aneurysm clip applier forcep 11.

In an alternative embodiment shown in FIGS. 9A, 9B and 9C, platform 42' is a small generally rectangular wedge extending radially outward from each of slits 40. The wedge is angled so that its height increases as one advances radially outwardly toward perimeter 33 of base 32 so as to raise coil 10 and arm portions 12 and 14 of each clip above the adjacent top surface 34.

Optical axis 61 for this embodiment will be tipped at an angle to the vertical so that optical axis will be perpendicular to angled surface 43 of wedge shaped platform 42'.

Coil portion 10 of clip 8 rests along the top surface 43 of platform 42'. Because of the angle of surface 43 only a portion of clip 8 touches surface 43.

Figure 10A:
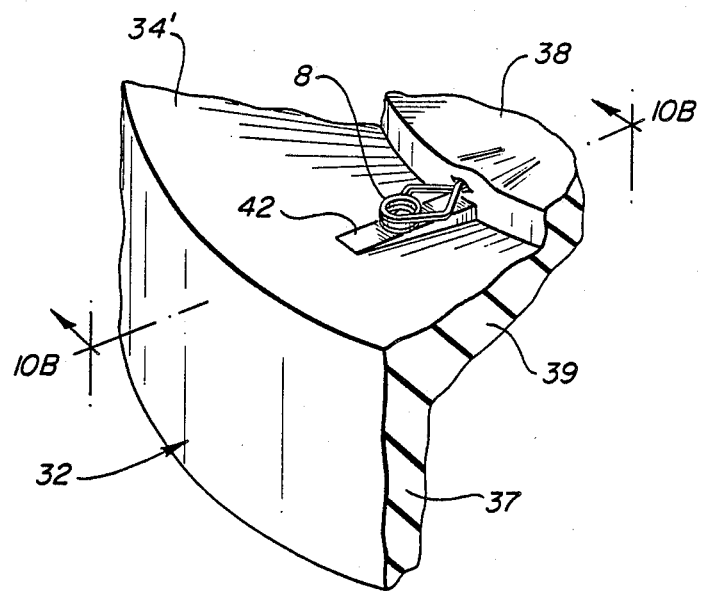
FIG. 10A shows a partial perspective view of a segment of another embodiment of the present invention; and, FIG. 10B shows a side elevational view partly in section taken along line 10B—10B in FIG. 10A.
Figure 10B:
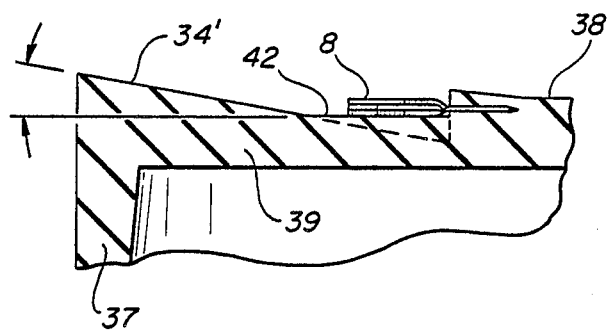

In the still further embodiment of the present invention shown in FIGS. 10A and 10B platform 42, which is similar to the platform shown in the embodiment of FIG. 8A extends generally radially outwardly from boss 38. In this embodiment top surface 34' of base 32 extends radially outwardly at an angle to the horizontal shown particularly in FIG. 10B. This angle is preferably about 10° but may be any convenient angle.

The preferred embodiment of the present invention as shown particularly in FIG. 2 shows five aneurysm clips. Any convenient number of aneurysm clips can be used together with a similar number of individual lenses. Alternatively, individual lenses 60 could be replaced by a single annular lens extending annular about magnifier housing 52.

The present invention has been described in conjunction with preferred embodiments. Those skilled in the art will appreciate that many modifications and changes may be made to the preferred embodiments without departing from the present invention. It is, therefore, not intended to limit the present invention except as set forth in the appended claims.

I claim:

1. A container and dispenser for a plurality of aneurysm clips comprising:
    a base for retaining a number of clips;
    clip retaining means on said base for holding said clips;
    platform means on said base aligned with said clip retaining means for separating at least a portion of each of said clips from said base to facilitate grasping said clip with an instrument;
    a magnifier housing;
    at least one lens in said magnifier housing in position to allow a user to visualize said platform means through said lens;
    cooperative means on said base and said magnifier housing for operatively connecting said base and said magnifier housing together to permit said magnifier housing to be moved between a first position and a second position separated from said platform means by the focal distance of said lens to bring the clips into focus for the user to facilitate the removal of clips from the dispenser.

2. The apparatus of claim 1 wherein said base is made of a resilient material.

3. The apparatus of claim 1 wherein said base is made of silicone.

4. The apparatus of claim 1 wherein said base includes a right circular cylinder.

5. The apparatus of claim 1 wherein said clip retaining means is integral with said base.

6. The apparatus of claim 1 wherein said platform means is integral with said base.

7. The apparatus of claim 1 wherein said clip retaining means includes a slit in said base for retaining at least a portion of a clip.

8. The apparatus of claim 1 wherein said platform means includes a wedge having an angled surface, the height of which increases as one advances from the center of said base toward the perimeter of said base.

9. The apparatus of claim 1 wherein said cooperative means for operatively connecting said base and said magnifier housing includes:
    a centrally disposed shaft extending from said magnifier housing and a corresponding bore in said base for slidably receiving said shaft so that said magnifier housing may be moved between said first and second positions.

10. The apparatus of claim 1 wherein said cooperative means operatively connecting said magnifier housing and said base includes a stop means for holding said magnifier housing at said second position.

11. A container and dispenser for a plurality of aneurysm clips comprising:
    a generally cylindrical base having a top surface and bottom and a generally circular cross section and made of a generally resilient material for retaining a number of aneurysm clips;
    a raised clip retaining boss coaxially aligned with said base and disposed on said base top surface and a plurality of slits in said boss for retaining a portion of each of said clips;
    platform means aligned with each of said slits on said base top surface for separating at least a portion of said clips from said base top surface;
    said base including a coaxially aligned bore;
    a magnifier housing;
    at least one lens in said magnifier housing aligned with each of said platforms;
    a shaft projecting from said magnifier housing and slidably engaging said base bore to permit said magnifier housing to be moved from a first position to a second position separated from said base by the focal distance of said lenses to bring said platform means into focus.

12. The apparatus of claim 11 wherein said magnifier housing includes a generally disc shape having a plurality of holes therethrough for receiving and supporting a corresponding plurality of lenses and wherein said shaft projects from one side of said disc and is coaxially aligned with said disc.

13. The apparatus of claim 11 wherein said platform means includes a wedge having an angled surface, the height of which increases as one advances from the center of said base toward the perimeter of said base.

14. The apparatus of claim 1 wherein said cooperative means cooperatively connecting said magnifier housing in said base include anti-rotation means to prevent said magnifier housing from readily rotating with respect to said base.

15. The apparatus of claim 1 wherein said base includes a portion extending from said clip retaining means to the perimeter to said base aligned at an angle to the surface of said platform means to facilitate the introduction of an instrument for grasping a clip.

* * * * *